(12) United States Patent
Fuller et al.

(10) Patent No.: US 10,653,515 B2
(45) Date of Patent: May 19, 2020

(54) TENDON REPAIR APPARATUS AND METHOD

(71) Applicants: MEDSTAR HEALTH, Washington, DC (US); THE CLEVELAND CLINIC FOUNDATION, Cleveland, OH (US)

(72) Inventors: Sam Fuller, Baltimore, MD (US); Dave Dudzinski, Strongsville, OH (US)

(73) Assignees: MEDSTAR HEALTH, Columbia, MD (US); THE CLEVELAND CLINIC FOUNDATION, Cleveland, OH (US)

( * ) Notice: Subject to any disclaimer, the term of this patent is extended or adjusted under 35 U.S.C. 154(b) by 345 days.

(21) Appl. No.: 15/592,675

(22) Filed: May 11, 2017

(65) Prior Publication Data
US 2017/0325935 A1  Nov. 16, 2017

Related U.S. Application Data

(60) Provisional application No. 62/336,865, filed on May 16, 2016.

(51) Int. Cl.
| | | |
|---|---|---|
| *A61F 2/08* | (2006.01) | |
| *A61B 17/064* | (2006.01) | |
| *A61B 17/11* | (2006.01) | |

(52) U.S. Cl.
CPC ............ *A61F 2/08* (2013.01); *A61B 17/0643* (2013.01); *A61B 17/1146* (2013.01);
(Continued)

(58) Field of Classification Search
CPC ........................................................ A61F 2/08
See application file for complete search history.

(56) References Cited

U.S. PATENT DOCUMENTS

| | | |
|---|---|---|
| 3,805,300 A | 4/1974 | Tascon-Alonso et al. |
| 4,519,392 A | 5/1985 | Lingua |
| (Continued) | | |

FOREIGN PATENT DOCUMENTS

| | | |
|---|---|---|
| WO | 9616612 | 6/1996 |
| WO | 2016061530 A1 | 4/2016 |

OTHER PUBLICATIONS

Search Report and Written Opinion for corresponding International Appln. PCT/US2017/032144, dated Jul. 25, 2017, pp. 1-13.

*Primary Examiner* — Matthew W Schall
(74) *Attorney, Agent, or Firm* — Tarolli, Sundheim, Covell & Tummino LLP

(57) ABSTRACT

A tendon repair apparatus includes a tendon bridge having oppositely disposed proximal and distal bridge ends spaced longitudinally apart by a bridge body. A plurality of engagement legs is provided. Each engagement leg has a proximal leg end attached directly to a corresponding one of the proximal and distal bridge ends and a distal leg end spaced transversely apart from the tendon bridge. At least one receiver plate, transversely spaced from the tendon bridge and extending substantially longitudinally and laterally parallel to the tendon bridge, is provided. The receiver plate includes a plurality of receiver apertures. Each receiver aperture corresponds to a selected engagement leg. Each receiver aperture is configured to selectively engage with a corresponding selected engagement leg. Engagement between the receiver aperture and the engagement leg maintains the receiver plate in transversely spaced indirect connection with the tendon bridge.

13 Claims, 10 Drawing Sheets

(52) U.S. Cl.
CPC ......... *A61B 2017/0641* (2013.01); *A61B 2017/0646* (2013.01); *A61F 2220/0016* (2013.01); *A61F 2250/0007* (2013.01)

(56) References Cited

U.S. PATENT DOCUMENTS

| | | | |
|---|---|---|---|
| 4,979,956 A | * | 12/1990 | Silvestrini |
| 5,800,544 A | * | 9/1998 | Demopulos ........ A61B 17/1146 606/53 |
| 5,916,224 A | | 6/1999 | Esplin |
| 6,083,244 A | | 7/2000 | Lubbers et al. |
| 7,361,179 B2 | | 4/2008 | Rousseau et al. |
| 8,114,129 B2 | | 2/2012 | Lubbers et al. |
| 8,480,692 B2 | | 7/2013 | McClellan |
| 8,888,398 B2 | | 11/2014 | Werth |
| 2012/0130374 A1 | | 5/2012 | Bouduban et al. |

* cited by examiner

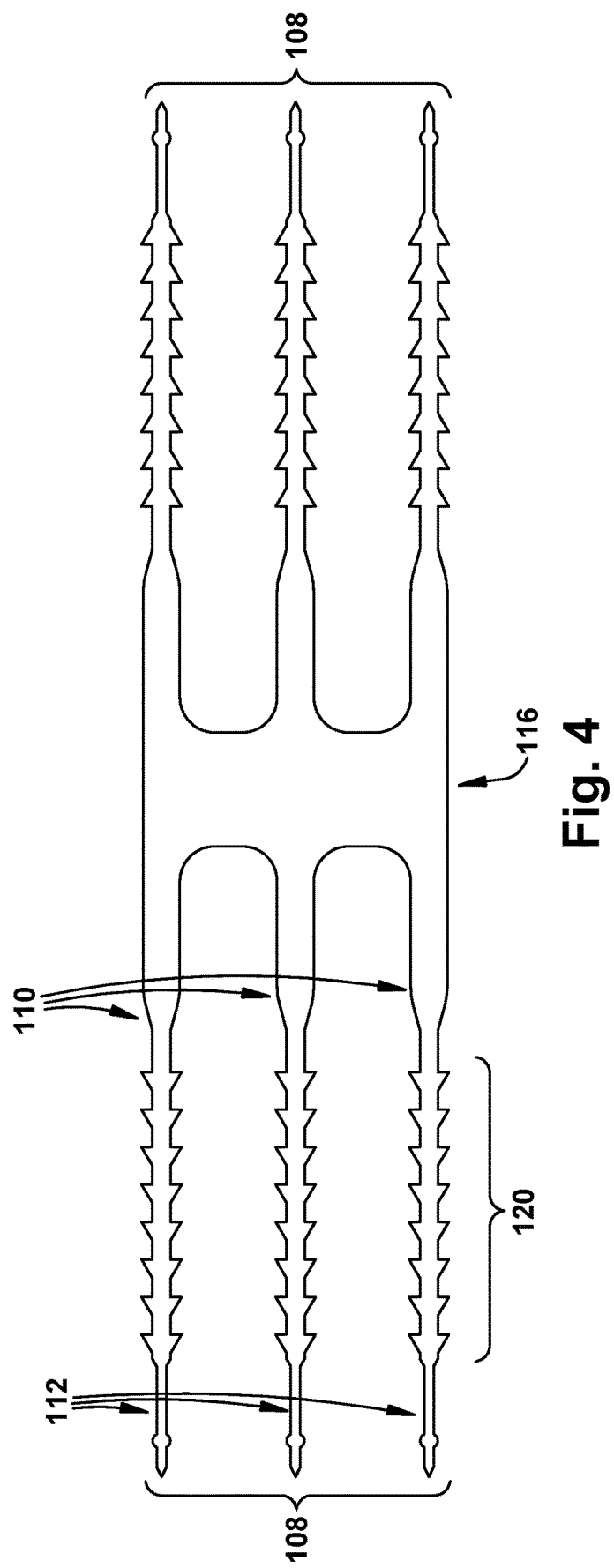

TENDON REPAIR APPARATUS AND METHOD

RELATED APPLICATION

This application claims priority from U.S. Provisional Application No. 62/336,865, filed 16 May 2016, the subject matter of which is incorporated herein by reference in its entirety.

TECHNICAL FIELD

This disclosure relates to a tendon repair apparatus and method.

BACKGROUND

A tendon is a soft, dense, regularly arranged connective tissue that attaches muscle to bone and is important for extremity function. Tendons are comprised of mostly type I collagen (80% by weight) that are arranged in fibrils. The fibrils form multiple fascicles within each tendon, which includes the basic tendon fibril and also fibroblasts in parallel rows. Covering the tendon is a thin fascia membrane called the epitenon layer. Tendons also contain some elastin fibers, a proteoglycan matrix, and proteinaceous filler between the connective tissue fibers.

When tendons are lacerated or rupture, they demonstrate poor spontaneous regenerative capabilities and complete regeneration is almost never achieved despite intensive remodeling. Because tendons are required to glide, they rely on their smooth fascial membrane sheath to cover the tendon while also allowing it to move and slide freely along adjacent tissue structures such as muscle, skin, narrow fibrous tunnels, other tendons, or bone. They are also simultaneously relied upon to resist tremendous forces acting upon them, and each tendon relies upon the strong fibril network to maintain its strength.

Patients whose tendon(s) are in discontinuity experience pain, reduced mobility, and overall decrease in function. End-to-end or end-to-side repair techniques can be useful in reattaching or reconstructing injured tendons. However, the timing of when to perform the repair and when to initiate the post-operative rehabilitation remains controversial. If the tendon repair is performed too late following the injury, the tendon edges may retract too far apart and a primary repair may not be able to be accomplished, and a tendon graft may be required. If the repair is performed in a timely manner, usually within seven to ten days, but the tendon rehabilitation is initiated too aggressively, gapping at the repair site or even early rupture of the repair site may occur. This is the result of initial weakness at the repair site due to the suture-repair technique for tendon repair. However, if rehabilitation is delayed in order to allow for the tendon to heal, then scarring and adhesions may form in the tendon sheath. This may result in decreased range of motion and, ultimately, poor function. In addition, because of the tight space within the tendon sheath, there is little room for scar tissue, suture, or additional apparatuses to hold the tendons together. Any additional bulk will decrease the gliding function of the tendon and lead to decreased range of motion, stiffness, and possible risk of rupture. This is present in all current treatments of tendon repairs, which include suture-based repairs.

SUMMARY

In an aspect, a tendon repair apparatus is described. A tendon bridge has oppositely disposed proximal and distal bridge ends spaced longitudinally apart by a bridge body. A plurality of engagement legs is provided. Each engagement leg has a proximal leg end attached directly to a corresponding one of the proximal and distal bridge ends and a distal leg end spaced transversely apart from the tendon bridge. At least one receiver plate, transversely spaced from the tendon bridge and extending substantially longitudinally and laterally parallel to the tendon bridge, is provided. The receiver plate includes a plurality of receiver apertures. Each receiver aperture corresponds to a selected engagement leg. Each receiver aperture is configured to selectively engage with a corresponding selected engagement leg. Engagement between the receiver aperture and the engagement leg maintains the receiver plate in transversely spaced indirect connection with the tendon bridge.

In an aspect, a method of providing a tendon repair is described. A tendon repair apparatus is provided. A tendon bridge has oppositely disposed proximal and distal bridge ends spaced longitudinally apart by a bridge body. A plurality of engagement legs is provided. Each engagement leg has a proximal leg end attached directly to a corresponding one of the proximal and distal bridge ends and a distal leg end spaced transversely apart from the tendon bridge. A first receiver plate is transversely spaced from the tendon bridge and extends substantially longitudinally and laterally parallel to the tendon bridge. The first receiver plate includes a plurality of receiver apertures. Each receiver aperture corresponds to a selected engagement leg. Each receiver aperture is configured to selectively engage with a corresponding selected engagement leg. Engagement between the receiver aperture and the engagement leg maintains the first receiver plate in transversely spaced indirect connection with the tendon bridge. A second receiver plate is transversely spaced from the tendon bridge and extends substantially longitudinally and laterally parallel to the tendon bridge. The second receiver plate includes a plurality of receiver apertures. Each receiver aperture corresponds to a selected engagement leg. Each receiver aperture is configured to selectively engage with a corresponding selected engagement leg. Engagement between the receiver aperture and the engagement leg maintains the second receiver plate in transversely spaced indirect connection with the tendon bridge. A target portion of a first tendon is accepted and maintained transversely between the first receiver plate and the proximal bridge end. The first tendon is at least partially penetrated with the first engagement leg. The first engagement leg is engaged with a corresponding receiver aperture of the first receiver plate. A target portion of a second tendon is accepted and maintained transversely between the second receiver plate and the distal bridge end concurrently with at least one of acceptance and maintenance of the first tendon between the proximal bridge end and the first receiver plate. The second tendon is at least partially penetrated with the second engagement leg. The second engagement leg is engaged with a corresponding second receiver aperture of the second receiver plate. The target portion of the first tendon and the target portion of the second tendon are simultaneously grasped with the tendon repair apparatus. With the tendon repair apparatus, the target portion of the first tendon and the target portion of the second tendon are held in a repair configuration.

BRIEF DESCRIPTION OF THE DRAWINGS

For a better understanding, reference may be made to the accompanying drawings, in which:

FIG. 4 is a top view of a component of the aspect of FIG. 1;

DESCRIPTION OF ASPECTS OF THE DISCLOSURE

Figure 1:
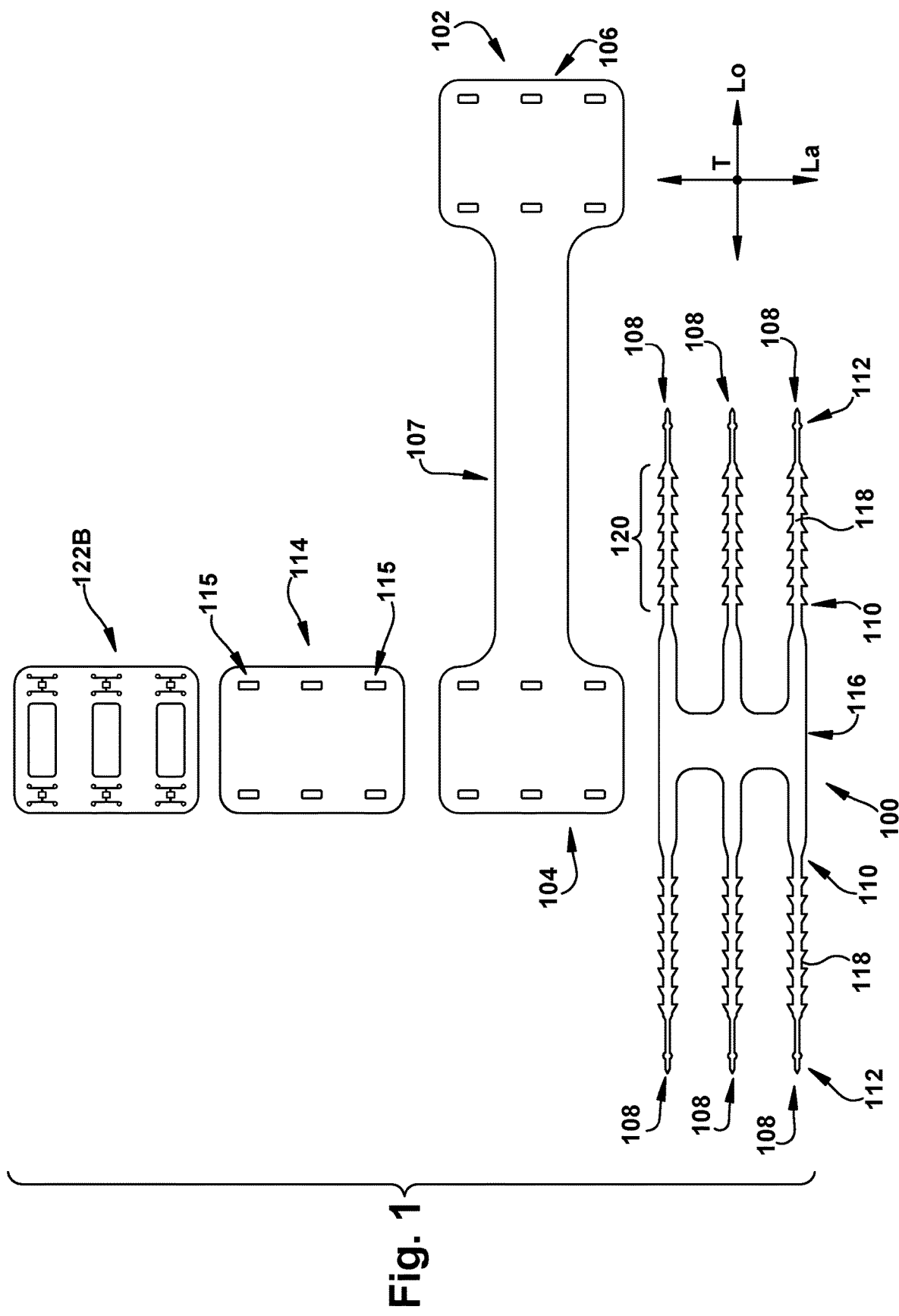
FIG. 1 is an exploded schematic view of an aspect of a tendon repair apparatus.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of an unconnected, broken, ruptured, or otherwise defective tendon. As such, treatment also includes situations where a defective tendon, or at least a symptom associated therewith, is completely inhibited, e.g., prevented from happening or stopped (e.g., terminated) such that the subject no longer suffers from the defective tendon, or at least the symptom(s) associated therewith. As used herein, the term "repair" includes joining, anastomosis, coaptation, approximation, connection, coupling, and any other suitable bringing-together of a body structure, such as a tendon, or portions thereof for the purpose of making a unitarily-functioning structure from two separate structures.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 2:
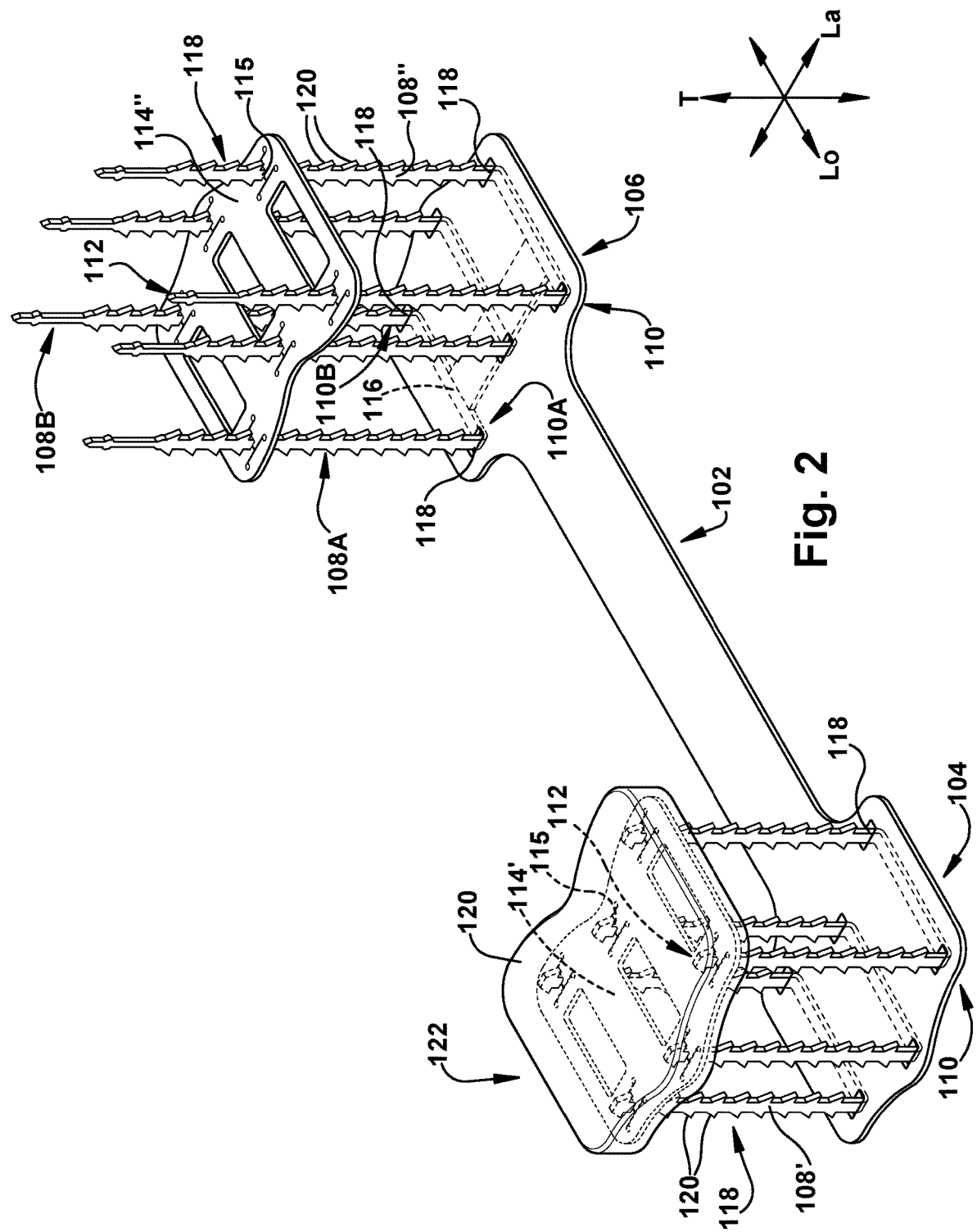
FIG. 2 is a perspective side view of the aspect of FIG. 1 in a partially assembled condition.

FIGS. 1-2 depict a tendon repair apparatus 100 which, generally, clamps together two tendons (or portions thereof) across a repair site while at the same time maintains a low-profile gliding function of the tendon, allowing immediate motion of the tendons after completion of the surgical procedure. In effect, the tendon repair apparatus 100 places a grasping component on each side of the tendon repair site, thereby bridging the gap between the tendon subcomponents through a low-profile apparatus. FIG. 1 is a sideways-exploded view, with the components of the tendon repair apparatus 100 shown in plan view in the order of assembly, and FIG. 2 depicts the tendon repair apparatus 100 at an intermediate stage of assembly.

As shown in FIGS. 1-2, a tendon bridge 102 has oppositely disposed proximal and distal bridge ends 104 and 106, respectively, spaced longitudinally apart by a bridge body 107. (The longitudinal direction is along arrow "Lo" in the Figures.) The overall length of the apparatus 100, or components thereof, may be chosen responsive to the dimensions of the tendon to be repaired or reconstructed. Optionally, and as shown in the Figures, the bridge body 107 may be narrower than the proximal and distal bridge ends 104 and 106. That is, the proximal and distal bridge ends 104 and 106 can both have a larger width in a lateral direction than a width of the bridge body 107 in the lateral direction. The lateral direction is perpendicular to the longitudinal direction (i.e., is along arrow "La") and is the top-to-bottom direction, in the orientation of FIG. 1. The tendon bridge 102 may be variable-length (not shown) in any suitable way, such as by including a telescoping and/or accordion-type feature allowing for longitudinal expansion and/or contraction of the tendon bridge 102 for custom-fitting to a particular use environment. Alternately, the tendon bridge 102, as with all components of the tendon repair apparatus 100, may have fixed dimensions (in this case, 10 mm, 16 mm, 20 mm, or any other suitable length).

A plurality of engagement legs 108 is provided. Each engagement leg 108 has a proximal leg end 110, attached directly to a corresponding one of the proximal and distal bridge ends 104 and 106, and a distal leg end 112 spaced transversely apart from the tendon bridge 102. The transverse direction is perpendicular to both the longitudinal and lateral directions (i.e., is along arrow "T") and is the up/down direction, in the orientation of FIG. 1.

At least one receiver plate 114 is transversely spaced from the tendon bridge 102 and extends substantially longitudinally and laterally parallel to the tendon bridge 102. The term "receiver plate" 114 is used herein to indicate the structure shown in the Figures, or any other component which is used to accept the engagement leg 108 after it passes through the tendon. The receiver plate 114 includes a plurality of receiver apertures 115. Each receiver aperture 115 corresponds to a selected engagement leg 108. Each receiver aperture 115 is configured to selectively engage with a corresponding selected engagement leg 108. Engagement between the receiver aperture 115 and the engagement leg 108 maintains the receiver plate 114 in transversely spaced indirect connection with the tendon bridge 102.

At least two spaced-apart engagement legs (examples labeled as 108A and 108B in FIG. 2) may have proximal leg ends 110A and 110B, respectively, connected directly together by a leg bridge 116. The leg bridge 116, when present, may directly contact and/or may be connected (e.g., fused, adhered, sealed, or otherwise attached, before or during the surgical procedure) to an underside of the tendon bridge 102—the underside being located transversely opposite the distal leg ends 112. In many use environments, it will be desirable to minimize a top-to-bottom dimension of the apparatus 100, so direct contact between the leg bridge 116 and the tendon bridge 102 could be desirable. It is also contemplated that, in some use environments, the leg bridge 116 could be attached to an upper side of the tendon bridge 102, so that the leg bridge 116 is directly transversely adjacent the tendon, with no tendon bridge 102 interposed therebetween.

Alternatively, the leg bridge 116 could be slightly spaced apart from the underside of the tendon bridge 102, optionally with an adhesive, pad, or other structure/substance interposed between the leg bridge 116 and the tendon bridge 102. The engagement legs 108A and 108B, in this situation, may extend through leg apertures 118 in the tendon bridge 102 to approximate the leg bridge 116 and the underside of the tendon bridge 102. The engagement legs 108 may be attached to the tendon bridge 102 in this manner to resist pull-out from the tendon bridge 102 under transverse tensile force. As shown in at least FIG. 1, the engagement legs 108 and leg bridge 116 may be integrally formed (e.g., stamped or laser-cut from sheet stock) as a single, flat piece, and the engagement legs 108 can then be bent transversely upward from the leg bridge 116 for engagement with other structures of the tendon repair apparatus 100 as shown and described herein. The presence of a "linking" or "connecting" leg bridge 116 does not affect the "end" status of the proximal leg end 110, which is described and considered herein to reference a particular region of the engagement leg 108, whether or not attached to a leg bridge 116.

As shown in the Figures, at least one engagement leg 108 may include a leg body 118 extending transversely between the proximal and distal leg ends 110 and 112, the leg body 118 including at least one serration 120 capable of enhancing engagement of the engagement leg 108 with a tendon into which at least a portion of the engagement leg 108 penetrates. For example, and as shown in the Figures, the engagement legs 108 may be significantly wider in the lateral direction than in the longitudinal direction, and may have serrations 120 on one or both lateral sides of the leg body 118. The serrations 120 may substantially extend in a transverse-lateral plane and "open" (widen) in a transversely downward direction, to enhance passage of the engagement legs 108 transversely upward through a tendon and resist pullout or motion of the engagement legs 108 transversely downward with respect to the tendon. To facilitate the insertions described herein, the serrations 120 can be structured to maintain deformation in the elastic range, and/or the serrations 120—or the entire engagement leg 108—could be made from a material which is more pliable or flexible than the materials of the other apparatus structures with which the serrations 120 interact, or may be made of the same material, such as NiTiNol.

As an example of an arrangement of the tendon repair apparatus 100, the receiver plate 114 may be a first receiver plate 114' (e.g., the "front" receiver plate in the orientation of FIG. 1), and the apparatus 100 may include a second receiver plate 114" (e.g., the "rear" receiver plate in the orientation of FIG. 1) longitudinally spaced from the first receiver plate 114'. Any number of receiver plates 114 can be transversely "stacked" as desired to achieve a predetermined locking strength of the apparatus 100 about the tendon(s). Similarly, a receiver plate 114 having a design similar to, or different than, that shown in the Figures could be provided by one of ordinary skill in the art to fulfill the "receiver plate" function in any desired use environment. It is also contemplated that an aspect of the apparatus 100 could omit the receiver plate 114 entirely, with the engagement legs 108 being simply held to the tendon by the serrations 120, by being bent or "tied" back down toward the tendon, or in any other desired manner.

At least a first engagement leg 108' is attached directly to the proximal bridge end 104 and at least a second engagement leg 108" is attached directly to the distal bridge end 106. The first engagement leg 108' maintains the first receiver plate 114' in transversely spaced indirect connection with the tendon bridge 102 concurrently with the second engagement leg 108" maintaining the second receiver plate 114" in transversely spaced indirect connection with the tendon bridge 102.

In any embodiment of the tendon repair apparatus 100, then, an optional receiver cap 120 may have a substantially similar shape in a longitudinal-lateral plane to a corresponding shape of the receiver plate 114. (E.g., the substantially round-cornered rectangle shape shown in FIG. 1, and/or the substantially elongated chevron shapes shown in FIG. 2, for the receiver cap 120 and receiver plate 114). An underside of the receiver cap 120 may be directly attached to an upper surface of the receiver plate 114, transversely opposite from the tendon bridge 102, as shown in FIG. 1. The receiver cap 120, when present, may be made from a material which is substantially less rigid than a material of the corresponding receiver plate 114. For example, if the receiver plate 114 is made from a metal such as Nitinol, the receiver cap 120 could be thin, low-profile, smooth silicone or a synthetic, low-profile polymer, which would assist in the gliding function of the tendon when the tendon repair apparatus 100 is in contact with adjacent structures and/or facilitate the "pseudo-tendon sheath" sliding of the tendon against the interior of the native tissue tendon sheath. The apparatus, which may be made of metal such as Nitinol or another material, may also be coated with another synthetic to further aid in the gliding function of the apparatus in the tendon sheath. Because of the tight confines within the native tissue tendon sheath and the need for longitudinal sliding of the repaired tendon against the interior of that native tissue tendon sheath, the low profile and relatively smooth outer surfaces of the tendon repair apparatus 100 assist with creating and supporting an end-to-end or end-to-side tendon repair to allow healing of the tendon with minimal scarring.

Optionally, when serrations 120 are provided to the engagement legs 108, at least one serration 120 may engage with an upper surface of the receiver plate 114 (i.e., a surface of the receiver plate 114 which is transversely opposite from the tendon bridge 102) to restrict movement of the receiver plate 114 transversely apart from the tendon bridge 102. Stated differently, and as shown in FIG. 2, the serrations 120 can penetrate through apertures 124 in the receiver plate 114 by motion of the engagement leg 108 in a transversely upward direction relative to the receiver plate 114, then the "flat" (laterally oriented) face of the serration 120 resists movement of the engagement leg 108 transversely downward with respect to the receiver plate 114. In other words, the combination of the serrations 120 and apertures 124 can be thought of as a one-way ratchet and pawl mechanism, with the addition of the receiver plate 114 and some protrusions on the pawl portion, as shown in at least FIG. 5. The small throughholes in the receiver plate 114 (i.e., the small holes at the end of the "cut" forming the cantilevered pawl portions surrounding the apertures 124) may help resist "backward" bending of the pawl portions and thus bolster the one-way holding strength of the ratchet/pawl mechanism formed by the serration/aperture combination. The pawls collectively defining each aperture 124 also include "fingers" which meet to form the longitudinal edges of the aperture 124 and thus prevent unwanted longitudinal motion of the engagement leg 108 with respect to the receiver plate 114.

Optionally, and particularly when the engagement legs 108 (like the rear engagement legs shown in FIG. 2) are originally significantly longer than a desired final lateral distance between the receiver plate 114 and the tendon bridge 102, the engagement legs 108 could be "trimmed" to length (like the front engagement legs shown in FIG. 2) once the final lateral spacing of the receiver plate 114 from the tendon bridge 102 is achieved. (The rearmost engagement legs in FIG. 2 maintain their original "spiked" tip profile, which may help with insertion through the tendon.) When present, the serrations 120 can serve as markers or indicators of length along the engagement leg 108. The leg body 118 could be cut or severed at the desired length (which will occur after the receiver plate 114 is engaged with the engagement legs 108). It is also contemplated that the serrations 120 could serve as frangible "break points" to allow the engagement legs 108 to be "snapped" off at the desired length. Optionally, this trimming of the engagement legs 108 to length will be done carefully, and/or include subsequent finishing steps, to result in substantially smooth trimmed distal leg ends 112 and thus avoid "catching" or snagging adjacent body tissues. It should be noted that, for the sake of this description, when an original distal leg end 112 (e.g., the spiked top profile on the rearmost engagement legs shown in FIG. 2) is trimmed, the portion of the leg body 118 which remains at the distalmost end of that engagement leg 108 will thereafter be considered to be the "new" distal leg end 112.

As previously mentioned, the receiver cap 122 could have a substantially similar shape in a longitudinal-lateral plane to a corresponding shape of the receiver plate 114. An underside of the receiver cap 122 may be directly attached to the upper surface of the receiver plate 114 in any desired manner, including adhesives and/or mechanical connection. For example, the receiver cap 122 may accept a distal leg end 112 (which could be a snapped- or cut-off top of a previously longer leg body 118) of at least one engagement leg 108.

Particularly if the receiver cap 122 is made of a softer material than the engagement leg 108, the distal leg end 112 could simply press into the receiver cap 122. Alternately, an aperture (not shown) could be provided in the receiver cap 122 to accept the distal leg end 112. Optionally, the serrations 120 of the engagement legs 108 could help resist pullout of the engagement legs 108 transversely downward from the receiver cap 122. For some use environments of the tendon repair apparatus 100, it will be undesirable for the engagement legs 108 to extend transversely through, and protrude from the top of, the receiver cap 122, so a smooth-surfaced receiver cap 122, such as that shown in FIG. 2, could be provided. A situation with an "extend-through" receiver cap 122, such as that shown in FIG. 1, will be described below with respect to FIGS. 6A-6B.

Optionally, though not shown in the Figures, a receiver cap may be provided on the underside of the tendon bridge 102. Such a "bottom" receiver cap may be attached to part or all of the tendon bridge 102 and may, similarly to the receiver caps 114 mentioned previously, assist with cushioning and gliding against adjacent native patient tissue structures.

Figure 3A:
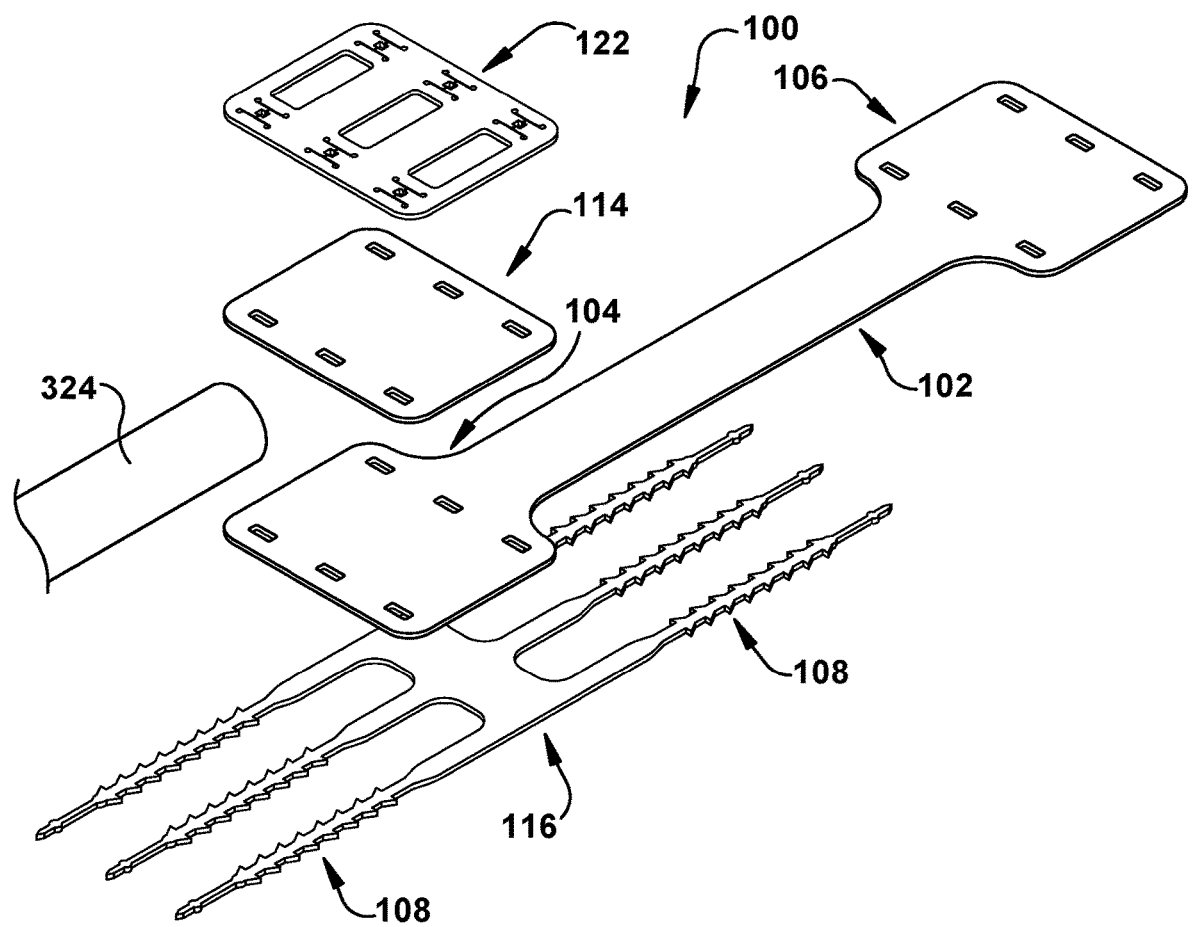
FIGS. 3A-3B are exploded perspective views of the aspect of FIG. 1 in alternate use configurations.
Figure 3B:
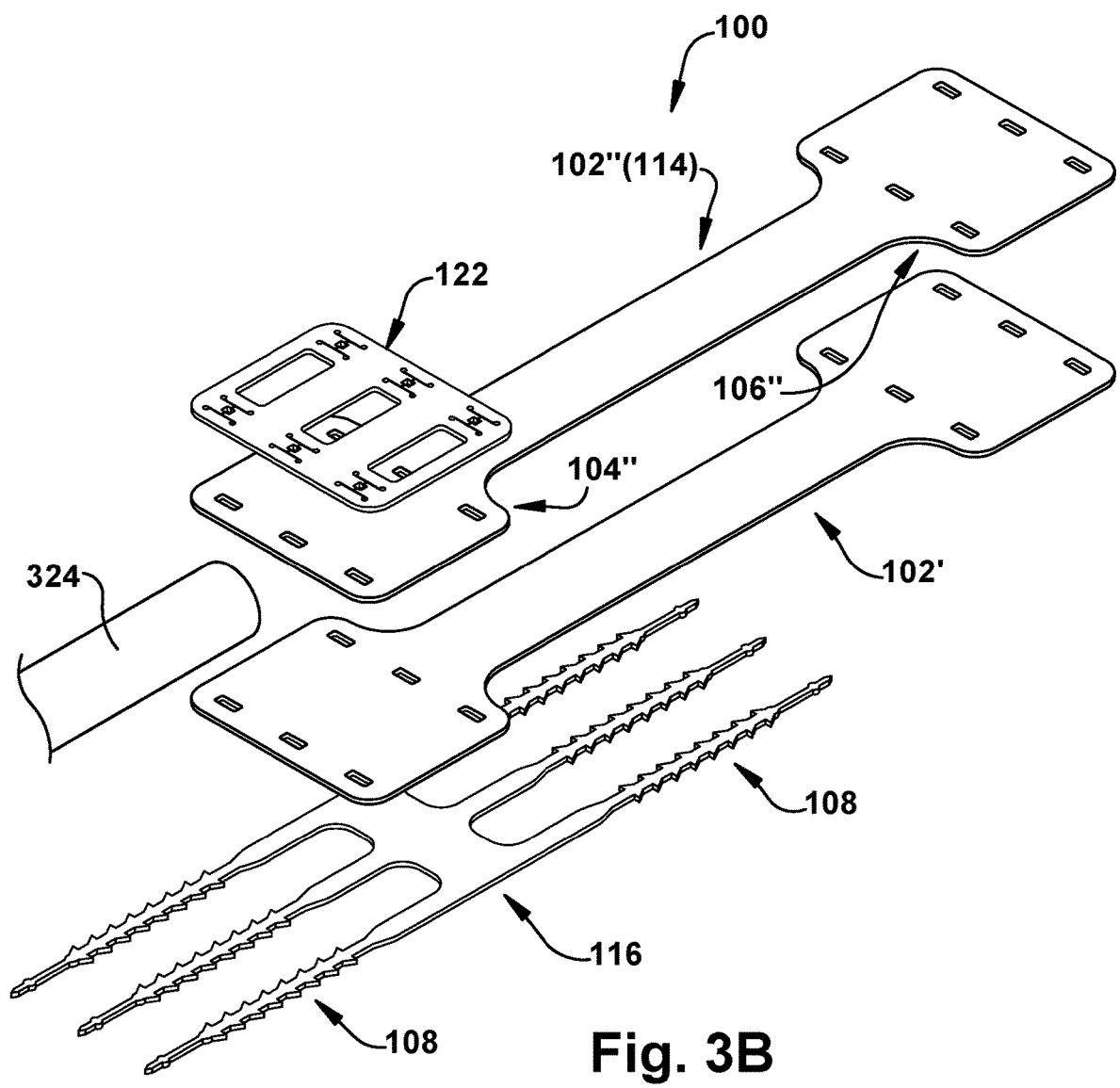

FIGS. 3A and 3B depict exploded use configurations for the tendon repair apparatus 100. In FIG. 3A, a tendon 324 is "sandwiched" transversely between a receiver plate 114 and a proximal bridge end 104 of a tendon bridge 102, with a receiver cap 122 being placed atop the receiver plate 114, such as to assist with retaining the engagement legs 108 (shown flattened in this view, but extending transversely upward from the leg bridge 116 in the final assembly configuration) through the tendon 324. In FIG. 3B, as another example of a use configuration, the tendon bridge 102 is a first tendon bridge 102', and the receiver plate 114 is the proximal bridge end 104" of a second tendon bridge 102". That is, in the FIG. 3B arrangement, the lower tendon bridge is a first tendon bridge 102', and a second tendon bridge 102" is provided, at least one of the proximal and distal bridge ends 104" and 106" of the second tendon bridge 102" being a receiver plate 114.

FIG. 4 depicts a plan view of a leg bridge 116, including a plurality of engagement legs 108, in a flattened format, before the engagement legs 108 are bent transversely (into or out of the plane of the page, in FIG. 4) at their proximal leg ends 110 to engage with a tendon 324 and receiver plate 114 and/or receiver cap 122. Six engagement legs 108 are shown in FIG. 4, though any desired number of engagement legs 108 could be provided by one of ordinary skill in the art for a particular use environment.

Figure 5:
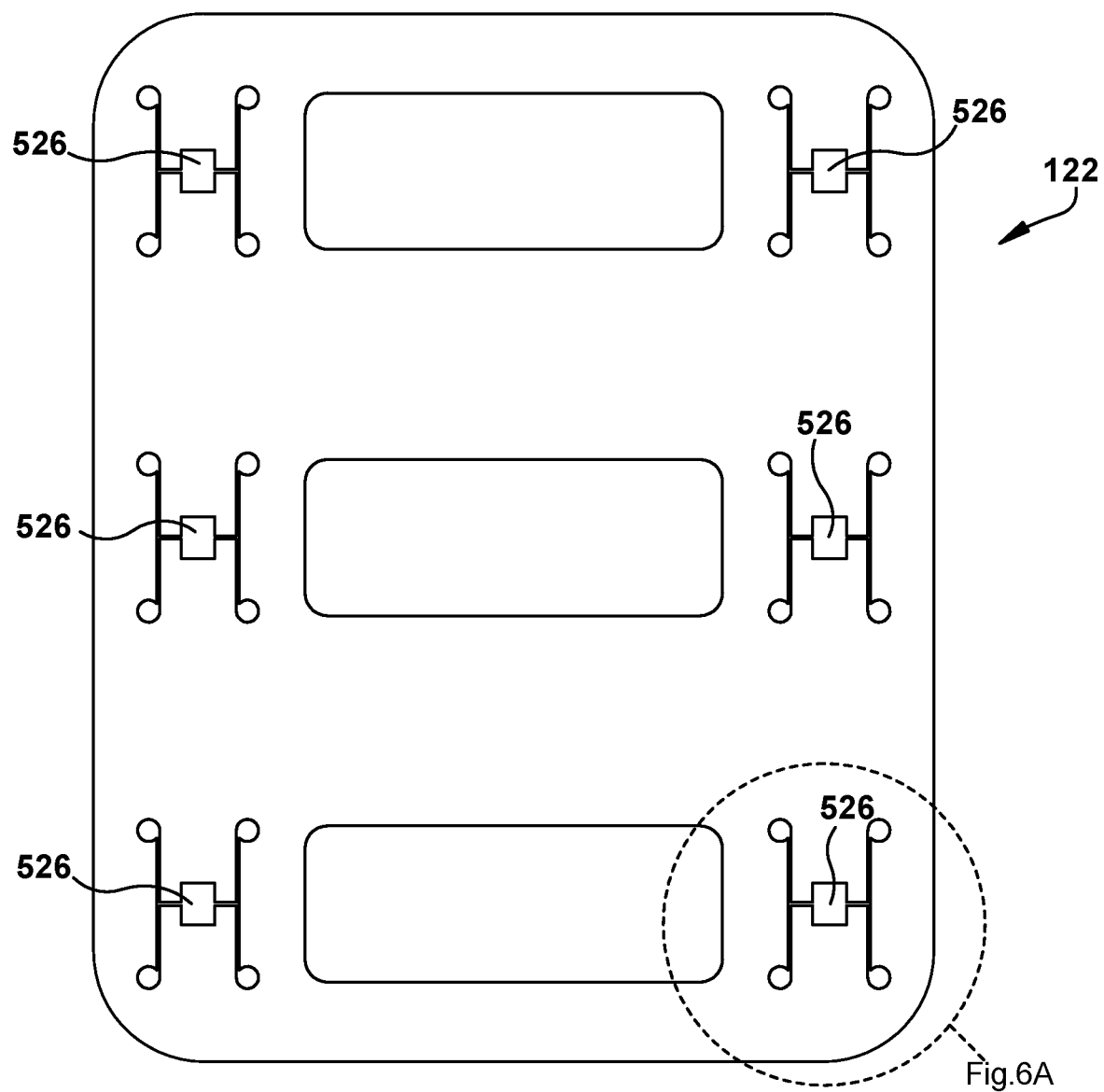
FIG. 5 is a top view of a component of the aspect of FIG. 1.

FIG. 5 is a plan view of a receiver cap 122 including a plurality (six shown) of cap apertures 526. Any desired number and configuration of engagement legs 108, receiver apertures 115, and cap apertures 526 can be provided by one of ordinary skill in the art, and these elements need not be matched in number for a particular tendon repair apparatus 100. Though the configuration of the cap apertures 526 will be described below in the context of a receiver cap 122, it is also contemplated that a similar configuration (though not shown) could be provided to one or more receiver apertures 115 of a receiver plate 114, whether or not the FIG. 5 configuration is simultaneously present on a corresponding receiver cap 122.

Figure 6A:
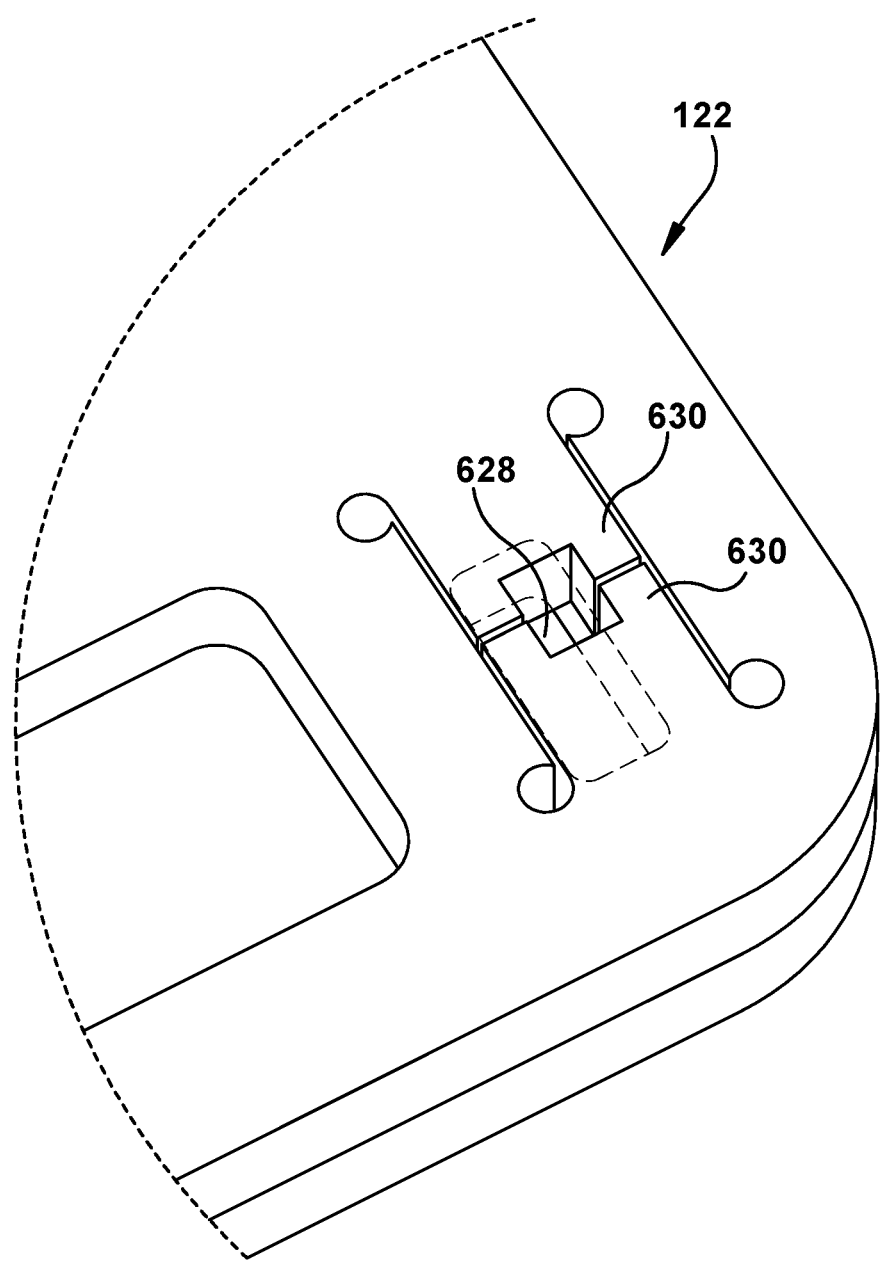
FIG. 6A is a detail view of area "FIG. 6A" of FIG. 5.
Figure 6B:
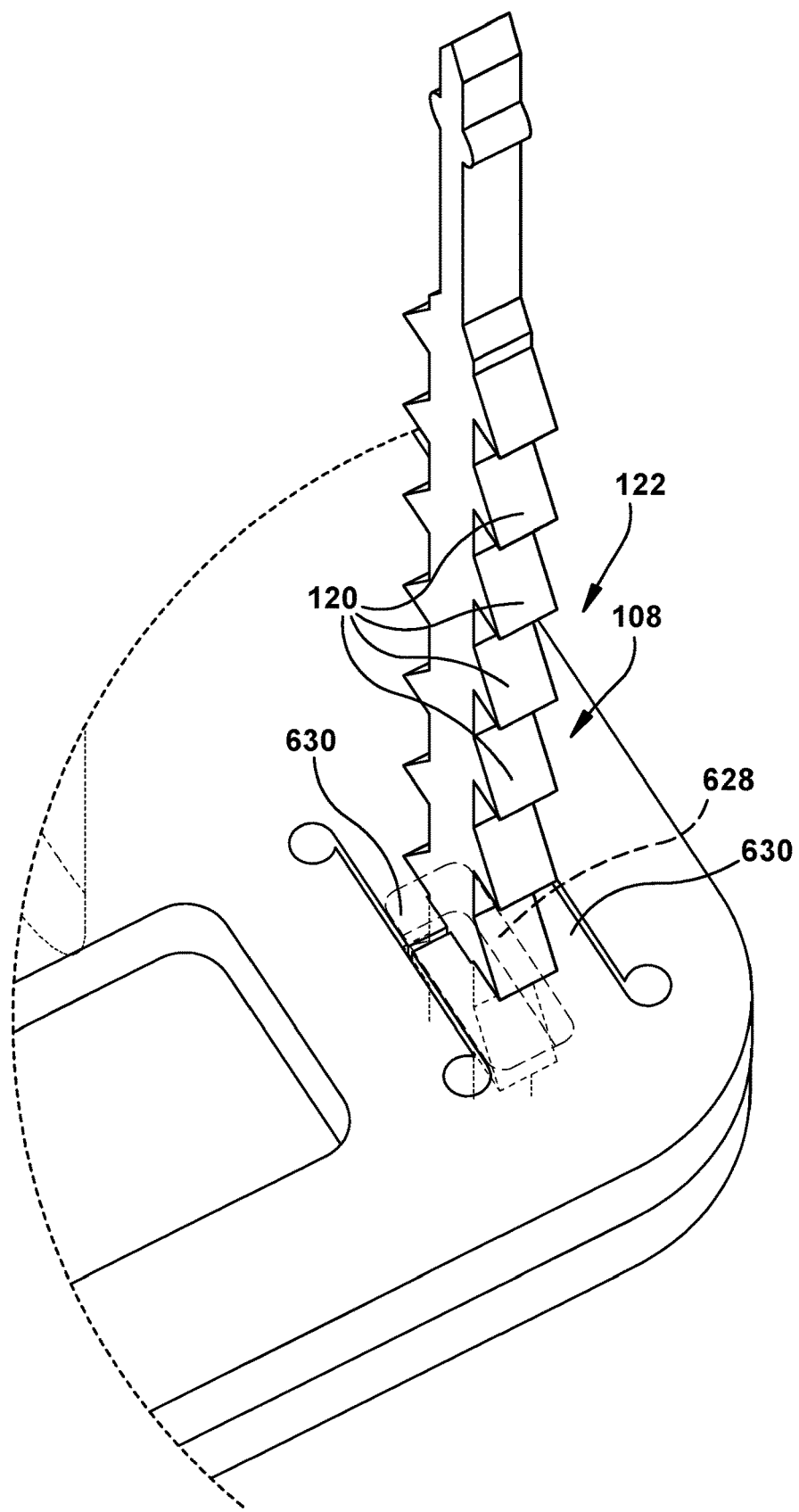
FIG. 6B is the detail view of FIG. 6A including another component of the aspect of FIG. 1.

As shown in FIGS. 6A-6B, which are detail views of area "FIG. 6A" of FIG. 5 which help to visually depict the ratchet/pawl arrangement previously mentioned, the cap apertures 526 include a central through-hole 628 which is formed cooperatively by cavities in two oppositely-facing aperture flaps 630. The aperture flaps 630 may include reduced-thickness "living hinge" areas (not shown), or may, as shown, simply be cantilevered from an adjacent portion of the material of the retainer cap 122. The aperture flaps 630, when present, may act in a "batwing door" type fashion, deflecting slightly to permit passage therethrough of an engagement leg 108, as shown in FIG. 6B, through the central through-hole 628. The central through-hole 628 will normally be smaller in total area than a maximum cross-sectional area (e.g., a cross-section taken in a lateral-longitudinal plane at the furthest/widest extent of a serration 120) of the leg body 118, to assist with selectively admitting, and securely retaining, the engagement leg 108 in the central through-hole 628.

Figure 7:
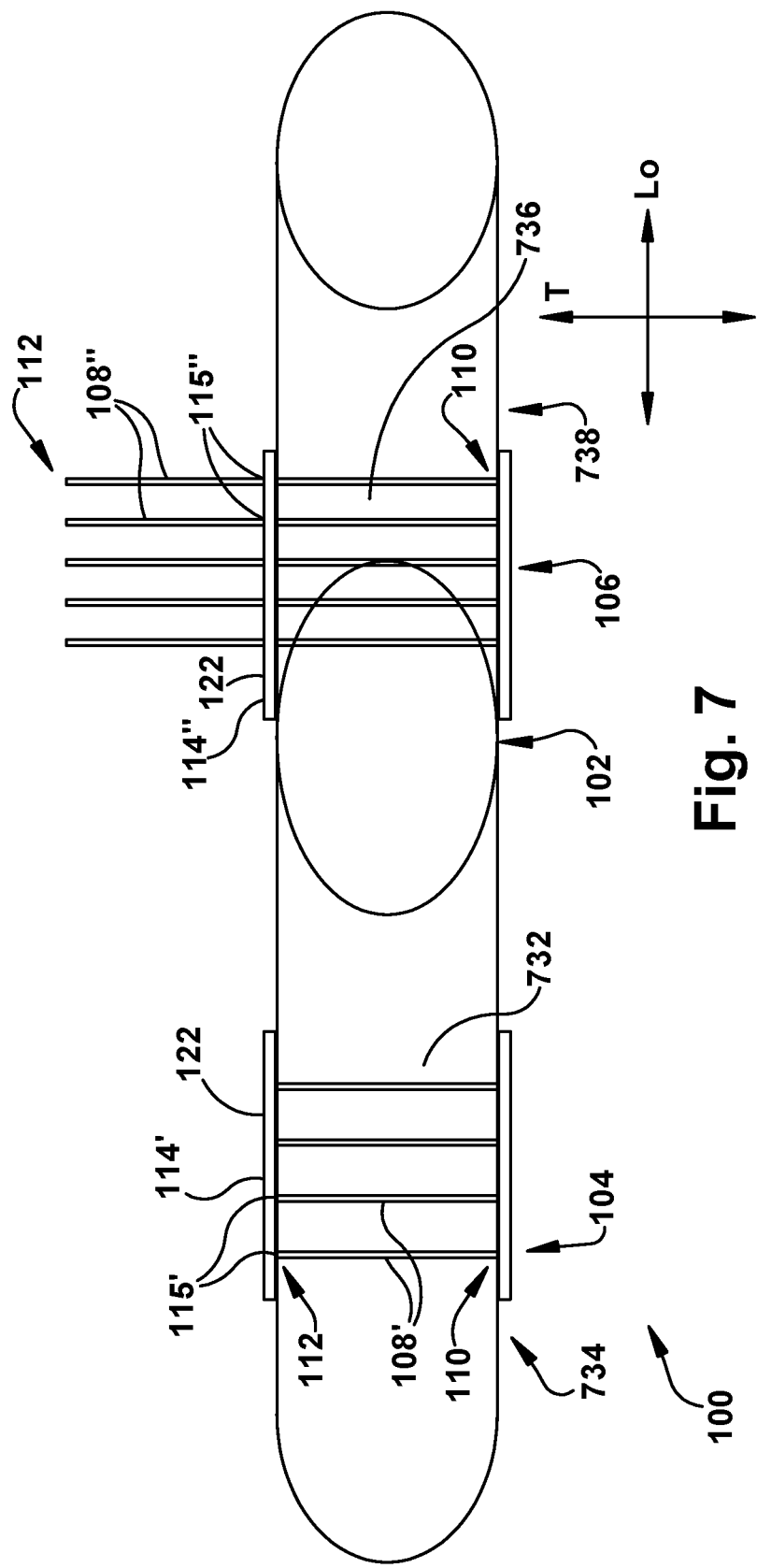
FIG. 7 is a schematic side view of the aspect of FIG. 1 in an example use environment.

As shown schematically in FIG. 7, the first receiver plate 114' and the proximal bridge end 104 may be configured to accept and maintain a target portion, such as the distal end 732 shown, of a first tendon 734 transversely therebetween, with the first engagement leg 108 at least partially penetrating the first tendon 734. The second receiver plate 114" and the distal bridge end 106 may be configured to accept and maintain a target portion, such as the proximal end 736 shown, of a second tendon 738 transversely therebetween concurrently with at least one of acceptance and maintenance of the first tendon 734 between the proximal bridge end 104 and the first receiver plate 114', with the second engagement leg 108" at least partially penetrating the second tendon 738.

Because the target portions are shown as the distal end 732 of the first tendon 734 and the proximal end 736 of the second tendon 738, FIG. 7 depicts an end-to-end tendon repair, and will be described as such for the sake of clarity. However, it is also contemplated that one of the first and second tendons 734 and 738 could have an end portion accepted by the tendon repair apparatus 100 for an end-to-side repair, thus that end portion would be approximated to a side portion of the other of the first and second tendons 734 and 738 in this alternate configuration example. One of ordinary skill in the art could readily provide any adaptations needed (including the mere shifting of positioning of the respective target portions) for use of the depicted and described tendon repair apparatus 100 for an end-to-side repair, an end-to-end repair, a weave repair, or any other desired use environment.

Through use of the tendon repair apparatus 100 as described and shown herein, a target portion (e.g., the distal end 225) of the first tendon 734 can be placed proximate to and/or in longitudinal contact with, a target portion (e.g., the proximal end 736) of the second tendon 738. This arrangement is facilitated and maintained through penetration of the engagement legs 108 through the first and second tendons 734 and 738, and encourages healing and melding together of the first and second tendons 734 and 738. It is contemplated that part or all of the tendon repair apparatus 100 may be biodegradable and/or bioabsorbable, for automatic degradation and/or removal of the apparatus 100 structures from the site following sufficient time for the tendon to heal together at the repair site. For example, a portion, such as the portion external to the tendon, of the tendon repair apparatus 100 could be bioabsorbable/biodegradable in order to facilitate tendon gliding (after degradation of a portion of the apparatus) while maintaining tendon strength, or the entire construct could be made of bioabsorbable/biodegradable material to substantially eliminate foreign body content from the repair site once sufficient time since the repair surgery has passed for the tendon to be self-supporting.

As previously mentioned, the tendon bridge 102 may be variable-length. In such case, the tendon bridge 102 may selectively shorten while the first engagement leg 108' is engaged with the first receiver plate 114' and the second engagement leg 108" is engaged with the second receiver plate 108", to be capable of applying tensile force to approximate the first and second tendons 734 and 738 into a repair configuration.

Figure 8:
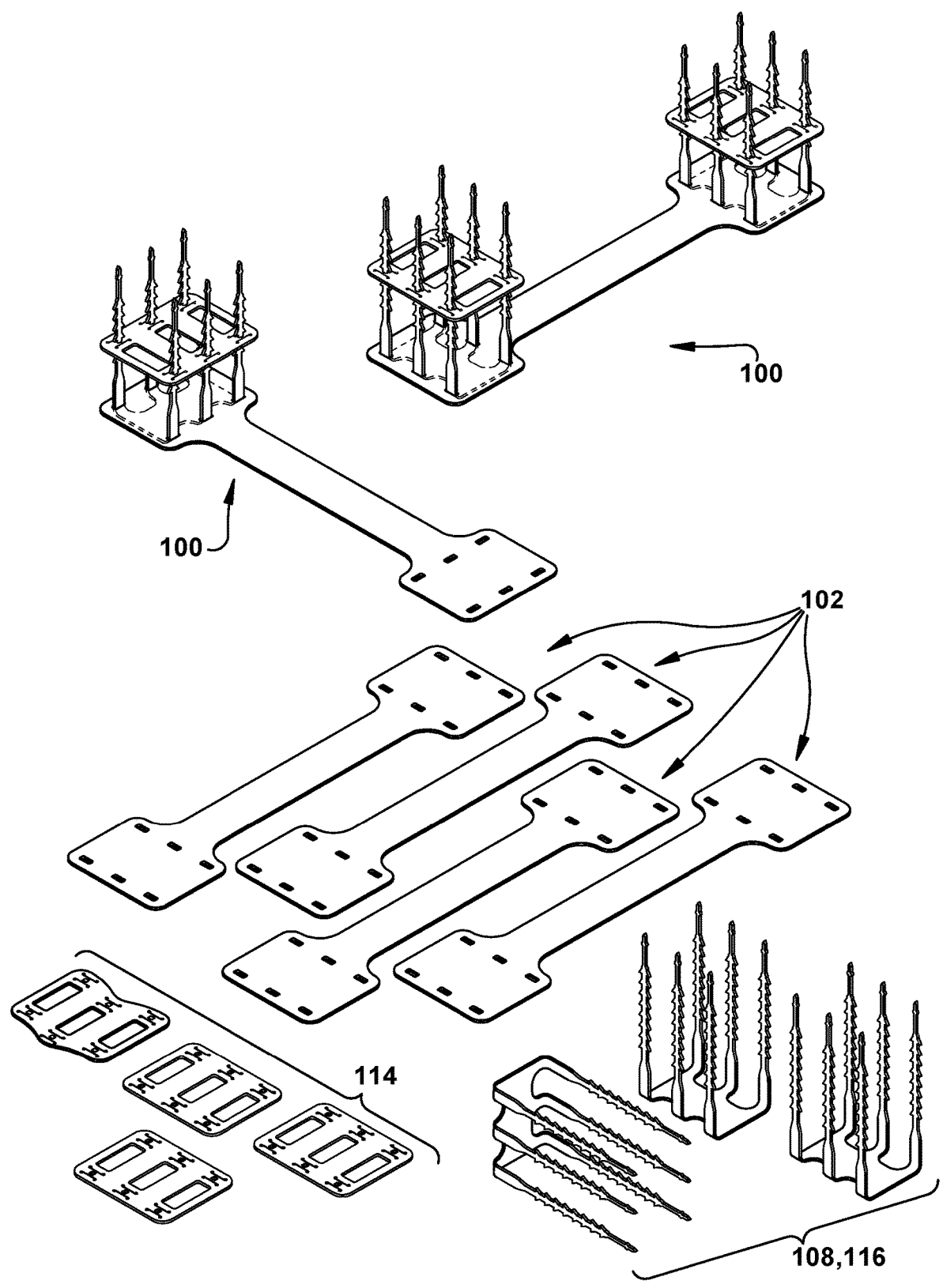
FIG. 8 depicts various examples of parts included in the aspect of FIG. 1.

FIG. 8 depicts a variety of assembled tendon repair apparatuses 100, along with an assortment of tendon bridges 102, receiver plates 114, and engagement legs 108 and leg bridges 116. It should be noted that variously shaped receiver plates 114 are shown in this Figure. FIG. 8 also includes leg bridges 116 which each hold more than two engagement legs 108, such that the entire complement of engagement legs 108 for a chosen proximal or distal bridge end 104 or 106 can be supplied simultaneously through manipulation of a single leg bridge 116.

A method of providing a tendon repair using the tendon repair apparatus 100 described and shown herein, then, includes accepting and maintaining the distal end 732 of the first tendon 734 transversely between the first receiver plate 114' and the proximal bridge end 104. The first tendon 734 is at least partially penetrated with the first engagement leg 108'. The first engagement leg 108' is engaged with a corresponding receiver aperture 115' of the first receiver plate 114'.

The proximal end 736 of the second tendon 738 is accepted and maintained transversely between the second receiver plate 114" and the distal bridge end 106 concurrently with at least one of acceptance and maintenance of the first tendon 734 between the proximal bridge end 104 and the first receiver plate 114'. The second tendon 738 is at least partially penetrated with the second engagement leg 108". The second engagement leg 108" is engaged with a corresponding second receiver aperture 115" of the second receiver plate 114".

The distal end 732 of the first tendon 734 and the proximal end 736 of the second tendon 738 are simultaneously grasped with the tendon repair apparatus 100. The tendon repair apparatus 100 thus holds the distal end 732 of the first tendon 734 and the proximal end 736 of the second tendon 738 in a repair configuration.

Once the first and second engagement legs 108' and 108" are engaged in the respective first and second receiver apertures 115' and 115", the distal leg ends 112 of the respective first and second engagement legs 108' and 108" are truncated to a length ending immediately adjacent to, and on a transverse side of, the corresponding first and second receiver plates 114' and 114".

When the tendon bridge 102 is variable-length, the method can include selectively shortening the tendon bridge 102 while the first engagement leg 108' is engaged with the first receiver plate 114' and the second engagement leg 108" is engaged with the second receiver plate 114", and applying tensile force to approximate the first and second tendons 734 and 738 into a repair configuration.

It is contemplated that an installation tool (akin to a stapler for installing staples) could be used to position the apparatus 100 or components thereof, engage the first and second tendons 734 and 738, and/or "finish" the installation of the tendon repair apparatus 100 in any desired manner.

It is also contemplated that one or more engagement legs could be bent back transversely downward into engagement with a tendon, or with another structure of the apparatus 100, after the initial passage transversely upward through the tendon, whether or not a receiver plate 114 is present. This "back-bending" may help to avoid catching/prominence of the engagement legs 108 with respect to the tendon, and also may assist with securement of the apparatus 100 to the tendon.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A tendon repair apparatus, comprising:
   a tendon bridge having oppositely disposed proximal and distal bridge ends spaced longitudinally apart by a bridge body;
   a plurality of engagement legs, each engagement leg having a proximal leg end attached directly to a corresponding one of the proximal and distal bridge ends and a distal leg end spaced transversely apart from the tendon bridge; and
   at least one receiver plate, transversely spaced from the tendon bridge and extending substantially longitudinally and laterally parallel to the tendon bridge, the receiver plate including a plurality of receiver apertures, each receiver aperture corresponding to a selected engagement leg, and each receiver aperture being configured to selectively engage with a corresponding selected engagement leg, engagement between the receiver aperture and the engagement leg maintaining the receiver plate in transversely spaced indirect connection with the tendon bridge;
   the receiver plate being indirectly connected to the tendon bridge only by at least one engagement leg.

2. The tendon repair apparatus of claim 1, wherein the tendon bridge is variable-length.

3. The tendon repair apparatus of claim 1, wherein the proximal and distal bridge ends both have a larger width in a lateral direction than a width of the bridge body in the lateral direction.

4. The tendon repair apparatus of claim 1, wherein at least two spaced-apart engagement legs have proximal leg ends connected directly together by a leg bridge, the leg bridge directly contacting an underside of the tendon bridge that is located transversely opposite the distal leg ends, the engagement legs extending through leg apertures in the tendon bridge to approximate the leg bridge and the underside of the tendon bridge.

5. The tendon repair apparatus of claim 1, wherein at least one engagement leg includes a leg body extending transversely between the proximal and distal leg ends, the leg body including at least one serration capable of enhancing engagement of the engagement leg with a tendon into which at least a portion of the engagement leg penetrates.

6. The tendon repair apparatus of claim 1, wherein the receiver plate is a first receiver plate and the apparatus includes a second receiver plate longitudinally spaced from the first receiver plate, wherein at least a first engagement leg is attached directly to the proximal bridge end and at least a second engagement leg is attached directly to the distal bridge end, and wherein the first engagement leg maintains the first receiver plate in transversely spaced indirect connection with the tendon bridge concurrently with the second engagement leg maintaining the second receiver plate in transversely spaced indirect connection with the tendon bridge.

7. The tendon repair apparatus of claim 1, including a receiver cap having a substantially similar shape in a longitudinal-lateral plane to a corresponding shape of the receiver plate, an underside of the receiver cap being directly attached to an upper surface of the receiver plate, transversely opposite from the tendon bridge.

8. The tendon repair apparatus of claim 7, wherein the receiver cap is made from a synthetic polymer material and the corresponding receiver plate is made from metal.

9. The tendon repair apparatus of claim 5, wherein the at least one serration engages with an upper surface of the receiver plate, transversely opposite from the tendon bridge, to restrict movement of the receiver plate transversely apart from the tendon bridge.

10. The tendon repair apparatus of claim 9, including a receiver cap having a substantially similar shape in a longitudinal-lateral plane to a corresponding shape of the receiver plate, an underside of the receiver cap being directly attached to the upper surface of the receiver plate, the receiver cap accepting a distal leg end of at least one engagement leg.

11. The tendon repair apparatus of claim 6, wherein the first receiver plate and the proximal bridge end are configured to accept and maintain a distal end of a first tendon transversely therebetween, with the first engagement leg being capable of at least partially penetrating the first tendon, the second receiver plate and the distal bridge end are configured to accept and maintain a proximal end of a second tendon transversely therebetween concurrently with at least one of acceptance and maintenance of the first tendon between the proximal bridge end and the first receiver plate, with the second engagement leg being capable of at least partially penetrating the second tendon.

12. The tendon repair apparatus of claim 11, wherein the tendon bridge is variable-length and selectively shortens while the first engagement leg is engaged with the first receiver plate and the second engagement leg is engaged with the second receiver plate, to be capable of applying tensile force to approximate the first and second tendons into a repair.

13. The tendon repair apparatus of claim 1, wherein the tendon bridge is a first tendon bridge, and wherein a second tendon bridge is provided, at least one of the proximal and distal bridge ends of the second tendon bridge being a receiver plate.

* * * * *